United States Patent [19]

Lattrell et al.

[11] 4,234,584
[45] Nov. 18, 1980

[54] SUBSTITUTED PHENYLPIPERAZINE DERIVATIVES

[75] Inventors: Rudolf Lattrell, Königstein; Wilhelm Bartmann, Bad Soden am Taunus; Hermann Gerhards, Hofheim am Taunus, all of Fed. Rep. of Germany

[73] Assignee: Hoechst Aktiengesellschaft, Frankfurt am Main, Fed. Rep. of Germany

[21] Appl. No.: 44,948

[22] Filed: Jun. 4, 1979

[30] Foreign Application Priority Data

Jun. 6, 1978 [DE] Fed. Rep. of Germany ....... 2824677
Dec. 14, 1978 [DE] Fed. Rep. of Germany ....... 2853996

[51] Int. Cl.³ .................. A61K 31/495; C07D 401/12
[52] U.S. Cl. ..................................... 424/250; 544/363; 544/373
[58] Field of Search ............ C07D/403/12; 544/363, 544/373; 424/250

[56] References Cited

U.S. PATENT DOCUMENTS

| | | | |
|---|---|---|---|
| 3,910,924 | 10/1975 | Tamura et al. | 424/258 |
| 3,929,793 | 12/1975 | Popelak et al. | 544/373 |
| 4,147,869 | 4/1979 | Nakagawa et al. | 544/363 |

*Primary Examiner*—Paul M. Coughlan, Jr.
*Attorney, Agent, or Firm*—Curtis, Morris & Safford

[57] ABSTRACT

Phenylpiperazine derivatives of the formula I

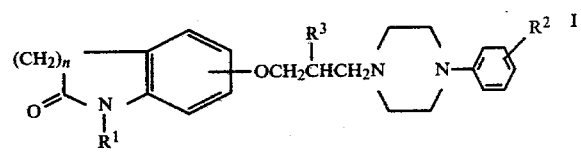

in which
R¹ denotes hydrogen or $C_1$–$C_6$ alkyl,
R² denotes hydrogen or one or several, identical or different substituents selected from the group of $C_1$–$C_6$-alkyl, $C_1$–$C_6$alkoxy, halogen, trifluoromethyl, hydroxy, nitro, amino and methylenedioxy,
R³ denotes hydrogen, hydroxy, $C_1$–$C_6$alkanoyloxy, and
n is 1 or 2, and the physiologically acceptable salts thereof, processes for their manufacture and medicaments containing or consisting of said compounds.

4 Claims, No Drawings

SUBSTITUTED PHENYLPIPERAZINE DERIVATIVES

The invention relates to novel, substituted phenylpiperazine derivatives and to processes for their manufacture. More particularly, it relates to novel phenylpiperazino-propyloxyindolinones and -quinolinones having valuable pharmacological and especially psychotropic properties and properties acting on the heart and cardiovascular system and, therefore, useful as medicaments.

It is, therefore, the object of the invention to provide phenylpiperazine derivatives of the formula I

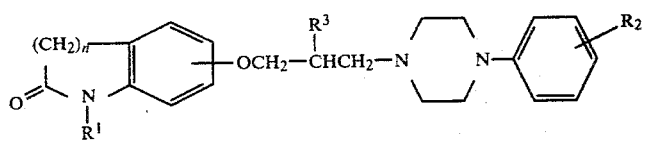

in which
  $R^1$ denotes hydrogen or $C_1$–$C_6$alkyl,
  $R^2$ denotes hydrogen or one or several, identical or different substituents selected from the group of $C_1$–$C_6$alkyl, $C_1$–$C_6$alkoxy, halogen, trifluoromethyl, hydroxy, nitro, amino and methylenedioxy,
  $R^3$ denotes hydrogen, hydroxy, $C_1$–$C_6$alkanoyloxy, and
  n is 1 or 2,
and the physiologically acceptable salts thereof.
Preferred substitutents are:
  for $R^1$ hydrogen and methyl;
  for $R^2$ hydrogen, methyl, ethyl, propyl, isopropyl, n-butyl, tert.butyl, methoxy, ethoxy, isoproxy, n-butoxy, fluorine, chlorine, bromine, iodine, trifluoromethyl, hydroxy, nitro and amino;
  for $R_3$ hydrogen, hydroxy, $C_1$–$C_4$alkanoyloxy, for example acetoxy, propionyloxy and trimethylacetoxy; and
  for n 1 or 2.

The present invention also provides processes for the manufacture of compounds of the formula I, which comprise
(a) reacting a compound of the formula II

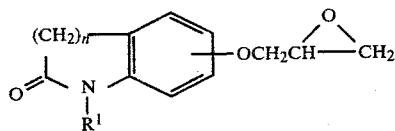

in which $R^1$ and n are as defined above, with a phenylpiperazine of the formula III

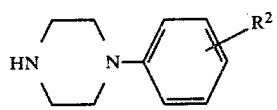

in which $R^2$ is as defined under formula I, whereupon compounds of formula I in which $R^3$ denotes hydroxy are obtained;
(b) reacting a compound of the formula IV

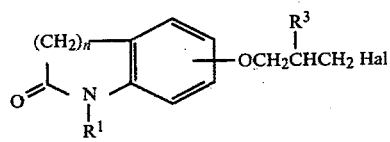

in which $R^1$, $R^3$ and n are as defined above and Hal denotes a halogen atom with a phenylpiperazine of the formula III;
(c) reacting a phenolic compound of the formula V

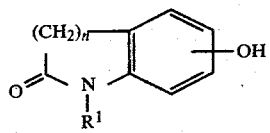

in which $R^1$ and n are as defined above, with a compound of the formula VI or VII

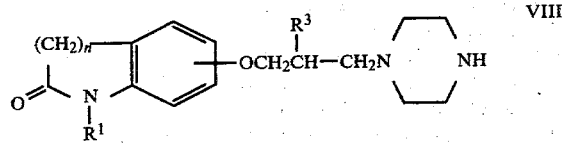

in which $R^2$, $R^3$ and Hal are as defined above;
(d) reacting a compound of the formula VIII

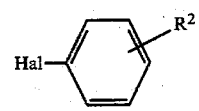

in which $R^1$, $R^3$ and n are as defined above, with a compound of the formula IX Hal—⌬—$R^2$  IX in which $R^2$ and Hal are as defined above;
(e) reacting a compound of the formula X

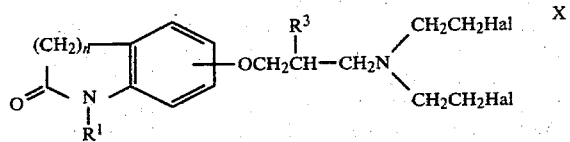

in which $R^1$, $R^3$, Hal and n are as defined above with a compound of the formula XI

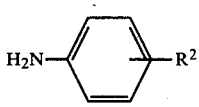

in which $R^2$ is as defined above;

(f) reacting a compound of the formula XII

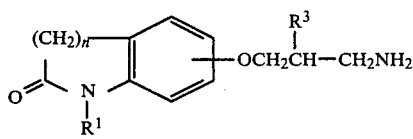

in which $R^1$, $R^3$ and n are as defined above with a compound of the formula XIII

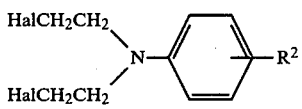

in which $R^2$ and Hal are as defined above; or (g) reacting a compound of the formula I in which $R^1$, $R^2$ and n are as defined under formula I and $R^3$ denoted hydroxy with an acylation agent of the formula Hal-CO-$C_1$-$C_6$alkyl or ($C_1$-$C_6$-alkyl-CO)$_2$O, whereupon a compound of the formula I in which $R_3$ denotes $C_1$-$C_6$alkanoyloxy is obtained.

According to process (a) the epoxide compound of formula II, prepared in known manner from a phenolic compound of formula V and epichlorohydrin, can be reacted with a phenylpiperazine of formula III in the absence of a solvent. If a solvent is used, the following are suitable: ethers such as tetrahydrofurane or dioxane; glycol ethers such a diglyme; aromatic hydrocarbons such as toluene, chlorobenzene; alcohols such as ethanol, isoamyl alcohol; aprotic solvents such as dimethyl formamide, dimethyl acetamide and the like. The reaction is carried out at a temperature in the range of from 30° to 200° C., preferably 50° to 160° C., preferably using equimolar amounts of the amine of formula III.

According to process (b) the 3-halopropoxy compound of formula IV, prepared in known manner, for example from an epoxide compound of formula II with a salt of a tertiary base, for example pyridine hydrochloride or, if $R^3$ denotes hydrogen, from a phenol of formula V and a 1,3-dihalopropane, is reacted with an amine of formula III, preferably in the presence of a base, such as sodium or potassium hydroxide, sodium or potassium carbonate, a tertiary amine such as triethyl amine or pyridine. It is also possible, of course, to operate in the absence of a base. In general, the reaction is carried out at a temperature in the range of from 50° to 200° C., preferably 60° to 160° C. If solvents are used for the reaction, all those listed above are suitable. The amine of formula III is used in an at least equimolar amount up to a five-fold molar excess.

According to process (c) the phenolic compound of formula V is reacted in known manner with a phenylpiperazine derivative of formula VI or VII, the reaction conditions being the same as those indicated above. According to a preferred embodiment, the phenolic compound of formula V is first converted into the corresponding alkali metal salt by means of an alkali metal alcoholate or hydride.

According to process (d) monosubstituted piperazine derivatives of formula VIII, prepared by processes (a) and (b) from compounds of formula II or IV and piperazine, are condensed with compounds of formula IX. The reaction is preferably carried out in a polar solvent, for example alcohols such as isoamyl alcohol, ethers such as diglyme, or aprotic solvents such as dimethyl formamide, at a temperature of from 60° to 200° C. in the presence of an acceptor for the hydrohalic acid formed during the course of the reaction, for example potassium carbonate.

According to process (e) a compound of formula X is condensed with an aniline derivative of formula XI in a solvent as defined above, at a temperature of from 60° to 160° C., preferably in the presence of a hydrogen halide acceptor, such as potassium carbonate or pyridine.

According to process (f) an aminopropanol compound of formula XII, prepared in known manner from compounds of formula II or IV, for example from the epoxides of formula II, with alcoholic ammonia solution, is condensed with a N-(bis-haloethyl)-aniline, under reaction conditions as defined for processes (d) and (e).

According to process (g) a compound of formula I in which $R^3$ denotes hydroxy is acylated in known manner, for example with an acid halide or acid anhydride.

The compounds of the formula I are isolated in free form or in the form of their salts, depending on the reaction conditions used. The free bases can be reacted with inorganic or organic acid and thus converted into their pharmacologically acceptable salts. Suitable acids are, for example, hydrochloric acid, sulfuric acid, phosphoric acid, aliphatic, alicyclic, araliphatic, aromatic, or heterocyclic carboxylic acids or sulfonic acids, for example acetic acids, tartaric acid, lactic acid, maleic acid, fumaric acid, citric acid, oxalic acid, methanesulfonic acid, hydroxyethanesulfonic acid, or synthetic resins containing acid groups.

The compounds according to the invention are novel and can be used as pharmacological agents. They have diverse effects, especially a neuroleptic and blood sugar-lowering action. Depending on the dose, they antagonize the amphetamine aggregation toxicity in mice ($ED_{50}$ values of from 0.5 to 20 mg/kg). In this test, groups of 10 mice each are kept in very narrow spaces (about 25 cm²/mouse) and one hour after administration of the active compound, each mouse gets an injection of 20 mg/kg of D-amphetamine subcutaneously in the form of a 0.2% aqueous solution. The dose is determined that protects 50% of the animals from death by amphetamine intoxication. Moreover, the compounds of the invention inhibit the fixation of tritium-labelled spiroperidol on constituents of the cell membrane of homogenized striated body (corpus striatum) rich in dopamine of rats and calves ($^3$H-spiroperiodal fixation test, J. Z. Fields et al., Brain Res. 136, page 578 (1977). The concentrations of the compounds necessary for a 50% inhibition ($IC_{50}$) are in the range of from $2.5 \times 10^{-6}$ to $1.0 \times 10^{-7}$ mols/liter.

Some of the compounds have no or a weak catalepotgenic effect only, that is to say they cause a cataleptic rigidity in rats in high doses only (>40 mg/kg).

The novel compounds can be administered per se or in admixture with physiologically tolerable excipients or carriers. They can be administered either orally, parenterally or intraveneously. For oral administration the active compounds of the invention are mixed with the substances commonly used for this purpose and brought in a suitable form of administration by usual methods, for example tablets, push-fit capsules, aqueous, alcholic or oily solutions. Suitable inert carrier materials are, for example, magnesium carbonate, lactose or corn starch with the addition of other substances, such as magnesium stearate. They can be formulated in the form of dry or moist granules. As oily carriers or solvents vegetable or animal oils can be used, for example sunflower oil or cod-liver oil.

Suitable solvents for the physiologically acceptable salts of the active compounds for an intraveneous administration are, for example, water, physiological sodium chloride solution or alcohols such as ethanol, propanediol or glycerol, as well as sugar solutions, for example of glucose or mannitol, or mixtures of the various solvents mentioned.

The compounds according to the invention and their pharmacologically acceptable salts exhibit their effect within a broad dosage range. The administered dose depends, of course, on the type of desired treatment, the mode of administration and the conditions, type and size of the mammal to be treated. Satisfactory results are obtained, in the case of oral administration, with doses of from 0.1 to 100 mg of active compound per kilogram of body weight of the animal. With human beings the daily dose varies from 20 to 800 mg of active substance, preferably 50 to 500 mg per man, with individual doses of from 20 to 200 mg, preferably one to 3 times per day. For intraveneous or intramuscular administration the dose ranges from 5 to 300 mg, preferably 10 to 200 mg daily.

The following examples illustrate the invention.

EXAMPLE 1

5-[3-<4-(2-Methoxyphenyl)-1-piperazinyl>-2-hydroxypropyloxy]-1-methyl-2-indolinone

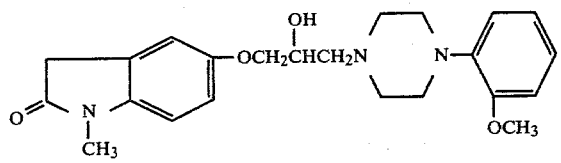

Process (a)

A mixture of 6.6 g (0.03 mol) of 5-(2,3-epoxipropyloxy)-1-methyl-2-indolinone and 5.8 g (0.03 mol) of 1-(2-methoxyphenyl)-piperazine in 10 ml of dioxane is kept for 2 hours at 100° C. After cooling, the mixture is diluted with 30 ml of diethyl ether.

A crystalline precipitate forms, which is filtered off with suction and washed with ether.

Yield: 10.6 g (86% of theory), melting point 96°-97° C.

The base is dissolved in acetone, a small excess of ethanolic hydrochloric acid is added, whereupon the dihydrochloride precipitates, which is filtered off with suction, washed with acetone and dried. Melting point 224°-226° C., yield quantitative.

Process (b)

The compound of Example 1 can also be prepared as follows: 0.26 g (0.01 mol) of 5-(3-chloro-2-hydroxypropyloxy)-1-methyl-2-indolinone, 0.3 g (0.015 mol) of 1-(2-methoxyphenyl)-piperazine and 1 g of potassium carbonate in 5 ml of N,N-dimethyl formamide are stirred for 48 hours at 120° C. After cooling, the mixture is diluted with 20 ml of water, the undissolved matter is filtered off with suciton and washed, first with water and then with ether. Melting point 96°-97° C., identical with the compound as obtained above.

Process (c)

0.01 Mol of sodium hydride and, at the end of the gas development, 2.7 g (0.01 mol) of 1-chloro-2-hydroxy-3-[4-(2-methoxyphenyl)-1-piperazinyl]-propane are added to 1.63 g (0.01 mol) of 5-hydroxy-1-methyl-2-indolinone in 20 ml of dioxane. The mixture is refluxed for 10 hours, cooled, diluted with water and extracted with methylene dichloride. After concentration, ether is added, the precipitate is filtered off with suction, washed with ether and dried. Melting point 95°-96° C., identical with the compound as obtained above.

Process (d)

3.5 g (0.01 mol) of 5-[3-(bis(2-chloroethyl)amino)-2-hydroxypropyloxy]-1-methyl-2-indolinone and 3.7 g (0.03 mol) of o-methoxyaniline in 30 ml of diglyme are heated for 10 hours to 150° C. The mixture is diluted with water, extracted with methylene dichloride and the solvent is removed in vacuo. In the manner described above, a crystlline compound is isolated from the residue; all properties of the compound are identical with those of the above compound.

Process (e)

A mixture of 2.4 g (0.01 mol) of 5-(3-amino-2-hydroxypropyloxy)-1-methyl-2-indolinone, 2.5 g (0.01 mol) of bis-N,N-(2-chloroethyl)-2-methoxy-aniline, 5 g of anhydrous potassium carbonate and 30 ml of N,N-dimethyl formamide is heated for 10 hours to 130° C. After cooling, the mixture is diluted with water and worked up as described above. The compound is identical with that of process (a).

EXAMPLE 2

5-[3-<4-(4-Chlorophenyl)-1-piperazinyl>-2-hydroxypropyloxy]-1-methyl-2-indolinone

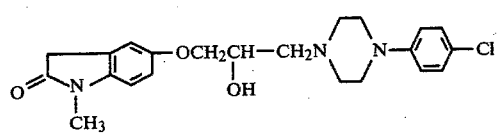

Process (a)

A mixture of 4.4 g (0.02 mol) of 5-(2,3-epoxipropyloxy)-1-methyl-2-idolinone and 3.9 g (0.02 mol) of 1-(4-chlorophenyl)-piperazine is heated for 45 minutes on the steam bath. The cooled, crystallized residue is triturated with ether, filtered off with suction and washed with ether.

Yield: 8.0 g (96 % of theory), melting point 144° C.

The dihydrochloride is prepared as described in Example 1, it melts at 202° C., the yield is quantitative.

EXAMPLE 3

5-[3-<4-(4-Chlorophenyl)-1-piperazinyl>-2-pivaloyloxypropyloxy]-1-methyl-2-indolinone

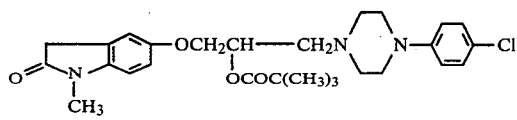

Process (g)

A mixture of 2.1 g (5 mmols) of 5-[3-<4-(4-chlorophenyl-1-piperazinyl>-2-hydroxypropyloxy]-1-methyl-2-indolinone, 5 g of pivalic acid and 5 g of pivalic anhydride is stirred for 4 hours at room temperature. The volatile constituents are removed under reduced pressure, the residue is dissolved in 30 ml of acetone. After addition of an excess amount of ethanolic hydrochloric acid, a crystalline precipitate forms, which is filtered off with suction, washed with acetone and dried. Yield: 2.0 g (80% of the theory). The dihydrochloride of the titel compound melts at 245° C. with decomposition.

EXAMPLE 4

5-[3-4-(2-Nitrophenyl)-1-piperazinyl/-2-hydroxypropyloxy]-1-methyl-2-indolinone

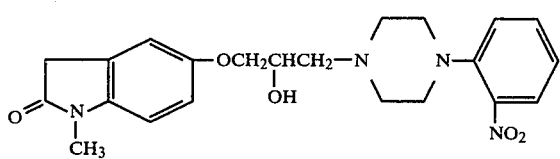

Process (d)

3 g (0.01 mol) of 5-[3-(1-piperazinyl)-2-hydroxypropyloxy]-1-methyl-2-indolinone, 1.7 g of o-chloronitrobenzene and 3 g of potassium carbonate in 30 ml of isoamyl alcohol are heated for 17 hours to 110° C. The solvent is removed under reduced pressure and the residue is treated with water and methylene dichloride. The solvent is removed under reduced pressure and the residue is dissolved in acetone. After addition of ethanolic hydrochloric acid, a precipitate forms, which is filtered off with suction and washed with acetone.

Yield: 4.1 g (87% of theory). The dihydrochloride melts at 233°–235° C. with decomposition.

EXAMPLE 5

5-[3-<4-(2-Aminophenyl)-1-piperazinyl>-2-hydroxypropyloxy]-1-methyl-2-indolinone

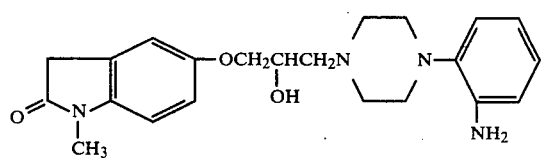

After addition of 0.5 g of Raney nickel, 2.5 g (3 mmols) of 5-[3-<4-(2-nitrophenyl)-1-piperazinyl>-2-hydroxypropyloxy]-1-methyl-2-indolinone dihydrochloride (Example 4) in 40 ml of methanol are hydrogenated with hydrogen at room temperature in an oscillating apparatus. After 1 hour, the calculated amount of hydrogen is absorbed. The Raney nickel is filtered off, the solvent is removed under reduced pressure, the crystalline residue is suspended in acetone, filtered off with suction and washed with acetone. Yield: 2 g (85% of theory). The dihydrochloride melts at 203°–206° C. with decomposition.

In a manner as described in Examples 1 to 4 the compounds listed in the following table I are prepared.

Table I

| Ex. No. | $R^1$ | indoline isomer* | $R^2$ | melting point of base or salt | °C. |
|---|---|---|---|---|---|
| 6 | $CH_3$ | 4 | 2-$CH_3O$ | 2 HCl | 226–228 |
| 7 | $CH_3$ | 6 | 2-$CH_3O$ | 2 HCl | 233–235 |
| 8 | $CH_3$ | 7 | 4-Cl | 2 HCl | 206–207 |
| 9 | $CH_3$ | 5 | H |  | 108–110 |
|   |   |   |   | 2 HCl | 176–178 |
| 10 | $CH_3$ | 5 | 3-$CH_3O$ | 2 HCl | 136–138 |
| 11 | $CH_3$ | 5 | 4-$CH_3O$ |  | 159 |
|   |   |   |   | 2 HCl | 224 |
| 12 | $CH_3$ | 5 | 2-$C_2H_5O$ | 2 HCl | 212–214 |
| 13 | $CH_3$ | 5 | 4-OH |  | 194 |
|   |   |   |   | 2 HCl | 200 |
| 14 | $CH_3$ | 5 | 2-Cl | 2 HCl | 180 |
| 15 | $CH_3$ | 5 | 3-Cl |  | 137–138 |
|   |   |   |   | 2 HCl | 251–253 |
| 16 | $CH_3$ | 5 | 2-$CF_3$ | 2 HCl | 270 |
| 17 | $CH_3$ | 5 | 3-$CF_3$ | 2 HCl | 190 |
| 18 | $CH_3$ | 5 | 4-F |  | 152 |
|   |   |   |   | 2 HCl | 230 |
| 19 | $CH_3$ | 5 | 2-$CH_3$ | 2 HCl | 250 |
| 20 | $CH_3$ | 5 | 2,6-di-$CH_3$ | 2 HCl | 256 |
| 21 | H | 5 | 2-$CH_3O$ | 2 HCl | 203 |
| 22 | H | 5 | 3-Cl | 2 HCl | 178 |
| 23 | H | 5 | 4-F | 2 HCl | 163 |

*position of the —OCH₂CH(OH)CH₂N⟨piperazinyl⟩—⟨C₆H₄⟩—R²— group at the benzene nucleus

EXAMPLE 24

5-[3-<4-(4-Chlorophenyl)-1-piperazinyl>-propyloxy]-1-methyl-2-indolinone

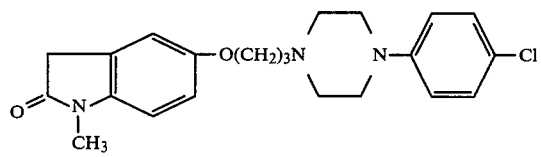

Stage 1: Preparation of 5-(3-bromopropyloxy)-1-methyl-2-indolinone

A mixture of 11.9 g of 5-hydroxy-1-methyl-2-indolinone, 29.2 g of 1,3-dibromopropane, 11 g of potassium carbonate, 1 g of potassium iodide and 75 ml of ethylmethyl ketone is refluxed for 20 hours. The mixture is then diluted with 300 ml of methylene dichloride, washed with water and the solvent is removed under reduced pressure.

The crude product obtained is filtered over silica gel (disactivated with 10% of water) with ethyl acetate:cyclohexane 1:1. After one run, an oil is eluted which is found to be uniform by thin layer chromatography and which can be directly used for further reaction.

Stage 2

2.8 g (0.01 mol) of 5-(3-bromopropyloxy)-1-methyl-2-indolinone, 2 g (0.01 mol) of 1-(4-chlorophenyl)-piperazine, 2.6 g of potassium carbonate and 20 ml of toluene are refluxed for 12 hours while stirring. The cooled mixture is diluted with 100 ml of methylene dichloride, washed with water and the solvent is removed under reduced pressure.

The amorphous residue of the organic phase is dissolved in 100 ml of acetone. After addition of an excess amount of ethanolic hydrochloric acid, a crystalline precipitate forms, which is filtered off with suction and washed with acetone.

Yield: 4.1 g (87% of theory) of dihydrochloride of the title compound melting at 170°–173° C. with decomposition.

In analogous manner the following derivatives are prepared from 5-(3-bromopropyloxy)-1-methyl-2-indolinone.

EXAMPLE 25

5-[3-<4-(2-Methoxyphenyl)-1-piperazinyl>-propyloxy]-1-methyl-2-indolinone

Yield: 92% of theory of dihydrochloride melting at 210°–211° C. with decomposition.

EXAMPLE 26

5-[3-<4-(3-Chlorophenyl)-1-piperazinyl>-propyloxy]-1-methyl-2-indolinone

Yield: 88% of theory of dihydrochloride melting at 205° C. with decomposition. Melting point of free base 107° C.

EXAMPLE 27

6-[3-<4-(4-Fluorophenyl)-1-piperazinyl>-2-hydroxypropyloxy]-1,2,3,4-tetrahydro-quinolin-2-one

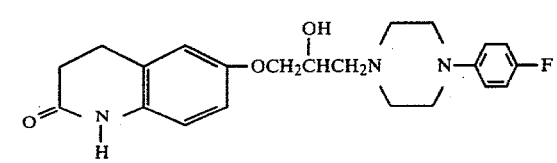

Process (a)

A mixture of 2.2 g (0.01 mol) of 6-(2,3-epoxipropyloxy)-1,2,3,4-tetrahydro-quinolin-2-one and 1.8 g (0.01 mol) of 1-(4-fluorophenyl)-piperazine is heated for 2 hours to 110° C. The cold residue is triturated with an acetone/ethyl acetate mixture 1:1, the crystal magma is filtered off with suction and washed with ethyl acetate.

Yield: 3.8 g (95% of theory), melting point 170° to 172° C.

The base is dissolved in acetone, a small excess amount of ethanolic hydrochloric acid is added, whereupon the dichloride separates. It is filtered off with suction, washed with acetone and dried. It melts at 220° C. with decomposition. The yield is quantitative.

Process (b)

The above product can also be obtained as follows: 0.25 g (0.01 mol) of 6-(3-chloro-2-hydroxy-propyloxy)-1,2,3,4-tetrahydroquinolin-2-one, 0.27 g (0.015 mol) of 1-(4-fluorophenyl)-piperazine and 1 g of potassium carbonate in 5 ml of N,N'-dimethyl formamide are stirred for 48 hours at 120° C. After cooling, the mixture is diluted with 20 ml of water, the precipitate is filtered off with suction and washed, first with water and then with a small amount of acetone. The compound melts at 168°–170° C. and is identical with the compound obtained by process (a).

The compounds indicated in the following Table II are prepared as described in Example 27 from 6-(2,3-epoxipropyloxy)-1,2,3,4-tetrahydroquinolin-2-one and the corresponding piperazine derivatives.

Table II

| Example No. | $R^2$ | base m.p. °C. | salt m.p. °C. |
|---|---|---|---|
| 28 | 3-Cl | amorphous | 130–135 |
| 29 | 4-Cl | 180–182 | 175–177 |
| 30 | 2-Cl | 139–140 | 230–232 |
| 31 | 2-$CH_3O$ | amorphous | 202–204 |
| 32 | 4-$CH_3O$ | amorphous | 224–226 |
| 33 | 2-$CF_3$ | amorphous | 226–227 |
| 34 | 3-$CF_3$ | amorphous | 200–202 |

EXAMPLE 35

6-[3-(4-(2-Methoxyphenyl)-1-piperazinyl)-propyloxy]-1,2,3,4-tetrahydro-quinolin-2-one

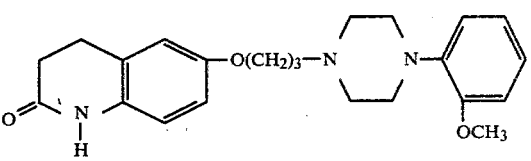

Stage 1: Preparation of 6-(3-bromopropyloxy)-1,2,3,4-tetrahydroquinolinone-2

A mixture of 11.9 g of 6-hydroxy-1,2,3,4-tetrahydroquinolin-2-one, 22.4 g of 1,3-dibromopropane, 11 g of potassium carbonate, 1 g of potassium iodide and 75 ml of ethylmethyl ketone are refluxed for 20 hours. The mixture is then diluted with 300 ml of methylene dichloride, washed with water and the solvent is removed under reduced pressure. The residue is triturated with ether, the crystals are filtered off with suction and washed with ether.

Yield: 8.6 g, melting point 113° to 114° C.

Stage 2

2.8 g (0.01 mol) of 6-(3-bromopropyloxy)-1,2,3,4-tetrahydroquinolinone-2, 1.92 g (0.01 mol) of 1-(2-methoxyphenyl)-piperazine, 4.2 g of potassium carbonate and 25 ml of toluene are refluxed for 5 hours. The mixture is diluted with methylene dichloride, washed with water and the solvent is removed under reduced pressure. The amorphous residue is dissolved in acetone, an excess amount of ethanolic hydrochloric acid is added, the precipitate formed if filtered off with suction and washed with acetone.

Yield: 4 g (85% of theory), melting point 190°–192° C. (dihydrochloride)

EXAMPLE 36

6-[3-<4-(4-Chlorophenyl)-1-piperazinyl>-propyloxy]-1,2,3,4-tetrahydroquinolin-2-one The compound is prepared as described in Example 35 from 6-(3-bromopropyloxy)-1,2,3,4-tetrahydroquinolin-2-one and 1-(4-chlorophenyl)-piperazine.

Yield: 80% of theory. Melting point of base 205°–206° C., of dihydrochloride 212°–214° C.

What is claimed is:

1. A phenylpiperazine compound of the formula

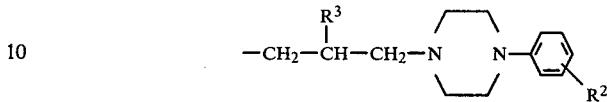

or a physiologically acceptable salt thereof, wherein
$R^1$ denotes hydrogen or $C_1$–$C_6$alkyl,
$R^2$ denotes one or several, identical or different, members selected from the group consisting of $C_1$–$C_6$-alkyl,
$C_1$–$C_6$alkoxy, halogen, trifluoromethyl, hydroxy, nitro, amino, and methylene-dioxy,
$R^3$ denotes hydrogen, hydroxy, $C_1$–$C_6$alkanoyloxy, and
n is 1 or 2.

2. A neuroleptic composition comprising a compound as defined in claim 1 and a physiologically acceptable auxiliary agent or carrier therefor.

3. The method of treating a human patient to produce a neuroleptic effect which comprises orally administering to said patient of a dose of about 20 to 800 mg/day of a compound as defined in claim 1.

4. The method of treating a human patient to produce a neuroleptic effect which comprises intravenously administering to said patient a dose of about 5 to 300 mg/day of a compound as defined in claim 1.

* * * * *